United States Patent
Furey et al.

(10) Patent No.: US 9,962,165 B2
(45) Date of Patent: May 8, 2018

(54) SYSTEM AND METHOD FOR DELIVERING MATERIAL INTO A PATIENT

(71) Applicant: COOK MEDICAL TECHNOLOGIES LLC, Bloomington, IN (US)

(72) Inventors: Aidan Furey, Copenhagen (DK); Anders Ginge Jensen, Hornslet (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 689 days.

(21) Appl. No.: 14/548,332

(22) Filed: Nov. 20, 2014

(65) Prior Publication Data

US 2015/0148779 A1   May 28, 2015

(30) Foreign Application Priority Data

Nov. 26, 2013 (GB) .................................. 1320830.1

(51) Int. Cl.
| | | |
|---|---|---|
| A61M 25/00 | (2006.01) | |
| A61M 29/00 | (2006.01) | |
| A61B 17/12 | (2006.01) | |
| A61B 17/00 | (2006.01) | |

(52) U.S. Cl.
CPC .... *A61B 17/12186* (2013.01); *A61B 17/1214* (2013.01); *A61B 17/12113* (2013.01); *A61B 17/12118* (2013.01); *A61M 25/0043* (2013.01); *A61B 2017/00004* (2013.01); *A61B 2017/00539* (2013.01); *A61B 2017/1205* (2013.01); *A61M 2025/0057* (2013.01); *A61M 2202/09* (2013.01)

(58) Field of Classification Search
CPC ........ A61B 17/12186; A61B 17/12118; A61B 17/1214; A61B 17/12113; A61B 2017/00004; A61B 2017/1205; A61B 2017/00539; A61M 25/0043; A61M 2202/09; A61M 2025/0057
USPC .................................................... 604/149, 284
See application file for complete search history.

(56) References Cited

U.S. PATENT DOCUMENTS 3,771,527 A * 11/1973 Ruisi .................... A61M 1/0084
                                                                              604/43
5,053,004 A * 10/1991 Markel ................ A61M 5/1582
                                                                              29/428

(Continued)

OTHER PUBLICATIONS

Extended European Search Report for EP14275157.7-1506 dated Apr. 7, 2015 (9 pages).

(Continued)

*Primary Examiner* — Julian W Woo
(74) *Attorney, Agent, or Firm* — Brinks Gilson & Lione (57) ABSTRACT

Apparatus for delivering material into a patient includes a catheter having a proximal end and a distal end. Material, preferably of filamentary or thread form, is fed from a material supply into a Y-fitting having a main branch and a side branch. The side branch is connected to a source of driving fluid able to feed drive fluid under pressure into the material carrier so as to pull material forwardly and out of the distal end of the catheter. The assembly includes an inner cannula within which material is passed from the material source. This increases the speed of delivery of material though the device and reduces the amount of drive fluid which is required.

16 Claims, 4 Drawing Sheets

(56) References Cited

U.S. PATENT DOCUMENTS

| | | | |
|---|---|---|---|
| 5,207,648 A * | 5/1993 | Gross | A61M 25/0014 604/164.09 |
| 5,221,255 A * | 6/1993 | Mahurkar | A61M 25/0028 604/43 |
| 5,833,652 A | 11/1998 | Preissman et al. | |
| 5,951,599 A * | 9/1999 | McCrory | A61B 17/12022 606/108 |
| 6,053,899 A | 4/2000 | Slanda et al. | |
| 6,146,373 A * | 11/2000 | Cragg | A61B 17/12022 604/19 |
| 6,312,421 B1 | 11/2001 | Boock | |
| 6,440,098 B1 | 8/2002 | Luscher | |
| 6,589,199 B1 | 7/2003 | McCrory et al. | |
| 7,771,387 B2 * | 8/2010 | Porter | A61B 17/00491 604/82 |
| 8,231,666 B2 * | 7/2012 | Kim | A61B 17/12022 623/1.11 |
| 2001/0041900 A1 | 11/2001 | Callister et al. | |
| 2003/0051735 A1 | 3/2003 | Pavcnik et al. | |
| 2005/0060017 A1 * | 3/2005 | Fischell | A61B 17/12022 623/1.11 |
| 2006/0147483 A1 | 7/2006 | Chaouk et al. | |
| 2008/0103477 A1 | 5/2008 | Jones | |

OTHER PUBLICATIONS

Examination Report for Application No. GB1320830.1, dated Sep. 22, 2015.
European Communication for EP 14275157.7-1501, dated Nov. 9, 2017 (5 Pages).

* cited by examiner

SYSTEM AND METHOD FOR DELIVERING MATERIAL INTO A PATIENT

CROSS-REFERENCE TO RELATED APPLICATIONS

This application claims the benefit of priority under 35 U.S.C. § 119(a) to Great Britain Patent Application No. 1320830.1, filed Nov. 26, 2013, which is incorporated by reference here in its entirety.

TECHNICAL FIELD

The present invention relates to apparatus and a method for delivering material into a patient, in the preferred embodiments to delivery of material endoluminally through a percutaneous entry point. The preferred embodiments can be used for filling an aneurysm, for closing a vessel or other organ, as well as for other medical procedures.

BACKGROUND ART

There are several medical conditions which can benefit from implantation into a patient of a filler material, an embolization or other device, whether temporary or permanent. Examples include the closure of blood vessels or other lumens so as to occlude these. One condition for which such procedures can be particularly useful is in the treatment of aneurysms, where a part of a vessel wall weakens and then expands outwardly to create an enlarged zone of the vessel, often having the form of a sac. This vessel expansion occurs as a result of blood pressure and tends to continue due to further and progressive weakening of the vessel wall. If left untreated, persistent pressure from the blood flow on the weakened wall tissue can lead to eventual rupture of the vessel wall and consequential haemorrhaging. Treatments for aneurysms have therefore focused on reducing the pressure on the weakened vessel wall, for instance by diverting blood flow or by isolating the weakened vessel wall for instance by means of a stent graft. Another treatment method involves filling the aneurysm sac with a filler material which stops the flow of blood into the sac and therefore stops or substantially reduces the pressure on the weakened walls. The filler may be an embolization coil, which will cause blood therearound to clot and thus close the sac and provide a protective barrier to prevent vessel rupture. In other instances, the aneurysm may be filled with a biocompatible material, such as a hydrogel or a polysaccharide fibre, which may be of a biodegradable nature. A biodegradable filler performs the same function as an embolization coil, that is to fill the aneurysm sac and provide pressure protection to the weakened vessel walls, with the additional advantage of allowing remodelling of the vessel wall over time. Moreover, biodegradation of the filler will ensure that no foreign matter remains in the patient's vessel after conclusion of the treatment.

Such fillers and coils can also be used to close off a vessel or other lumen in a patient.

The process of introducing such a filler or coil into a patient can take time, particularly given that this is often carried out remotely from the aneurysm by an endoluminal procedure.

Examples of prior art devices and methods can, for instance, be found in U.S. Pat. No. 6,312,421, US-2006/0147483, U.S. Pat. No. 6,589,199, U.S. Pat. No. 6,440,098.

SUMMARY OF THE INVENTION

The present invention seeks to provide an improved apparatus, assembly and method for delivering material into a patient and in the preferred embodiments into a vessel or aneurysm sac.

According to an aspect of the present invention, there is provided an assembly for delivering material into a patient including: an introducer unit having a proximal end, a distal end and a lumen extending within the introducer unit from the proximal to the distal ends; a side feed located at a position between the proximal and distal ends of the introducer unit and in fluid communication with the lumen; a material source coupled at the proximal end of the introducer unit, material thereof being passable through the lumen to the distal end of the introducer unit; and a driving fluid source coupled to the side feed; wherein supply of driving fluid through the side feed causes material in the lumen to be pulled towards and out of the distal end of the introducer unit.

The assembly provides a system which is able to feed material into a patient substantially faster than prior art systems and with the use of less driving fluid. The preferred embodiments are able to supply therapeutic quantities of material within a few seconds, often within a second or so, rather than over much longer time periods necessary with the prior art.

The assembly is particularly useful for feeding fibrous or filamentary material into a patent, such as into a vessel or aneurysm sac. Examples of suitable material include SIS (small intestine submucosa), polysaccharide, a biocompatible polymeric thread or other biocompatible material.

The introducer unit may be a single component or may, as in the embodiments described below, include a catheter and a proximal fitting which provides the side feed as well as the proximal end of the lumen. In the embodiments described below, the introducer unit is formed of a catheter and a Y-fitting attached to the proximal end of the catheter. The lumen extends through one branch of the Y-fitting and the catheter.

Advantageously, the side feed is disposed adjacent the proximal end of the catheter and is preferably oriented at an acute angle to the longitudinal axis.

The side feed acts to generate a stream of driving fluid within the lumen which pulls the material through the lumen by means of the pressure and flow of fluid from the side feed. In this regard, the material need not be separately fed into the lumen and can be simply disposed on a material carrier, such as a spool or the like, or in loose form in the material source.

Preferably, the assembly includes a cannula disposed in the introducer unit at the proximal end thereof; the cannula being coupled to the material feed.

The cannula preferably extends beyond a junction of the side feed and the lumen.

Advantageously, the cannula includes at least one aperture therein, driving fluid being able to pass into the cannula or inner catheter through said at least one aperture.

The cannula provides a passage for material into the lumen and can generate through the apertures jets of driving fluid for driving the material through the lumen and out of the distal end thereof.

Preferably, the cannula is shorter than the lumen, in practice most preferably extending only a short distance beyond the side feed.

The assembly preferably includes a sealed chamber between the driving fluid supply and the apertures in the cannula, the chamber acting to build pressure in the driving fluid.

The driving fluid source includes a fluid pump, advantageously a syringe.

According to another aspect of the present invention, there is provided apparatus for delivering material into a patient including: an introducer unit having a proximal end, a distal end and a lumen extending within the introducer unit from the proximal to the distal ends; a side feed located at a position between the proximal and distal ends of the introducer unit and in fluid communication with the lumen; the proximal end of the introducer unit being couplable to a material source such that material from the source is passable through the lumen to the distal end of the introducer unit; the side feed being couplable to a driving fluid source, wherein supply of driving fluid through the side feed causes material in the lumen to be pulled towards and out of the distal end of the introducer unit.

According to another aspect of the present invention, there is provided a method of delivering material into a patient by means of apparatus including an introducer unit having a proximal end, a distal end and a lumen extending within the introducer unit from the proximal to the distal ends; and a side feed located at a position between the proximal and distal ends of the introducer unit and in fluid communication with the catheter lumen; the method including the steps of: feeding a material from a material source coupled at the proximal end of the introducer unit, said material passing through the lumen to the distal end of the introducer unit; and driving a fluid through the side feed, said driving fluid causing material in the lumen to be pulled towards and out of the distal end of the introducer unit.

The material is advantageously fed through the lumen into a vessel or organ of a patient to close at least a part of said vessel or organ. An example provides for closure of an aneurysm sac.

Other features of the apparatus and method disclosed herein will become apparent from the following specific description of preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are described below various embodiments of apparatus and assembly for feeding material into a patient. The teachings herein are particularly useful for feeding blocking material into an aneurysm sac of a weakened vessel, so as to close off the aneurysm sac to blood flow and consequentially blood pressure. The apparatus can also be used to supply material to occlude a vessel, for example. The material can be of a type which permanently remains in the patient, thus as a permanent closure or occlusion device, or may be bioresorbable or biodegradable, allowing tissue remodelling over time. In the case of aneurysm treatment, once pressure is removed from within the aneurysm sac the weakened wall tissue will often heal, strengthen and remodel. In such cases, it is not necessary to maintain a sac filler.

The embodiments described below are able to provide very rapid delivery of material through the catheter and tests have shown that therapeutically sufficient amounts can be delivered within times of just a few seconds, often no more than around one second. This is much faster than prior art devices. Moreover, the apparatus requires less driving fluid compared to prior art systems, as a result of much more efficient driving of the material through the catheter.

Figure 1:
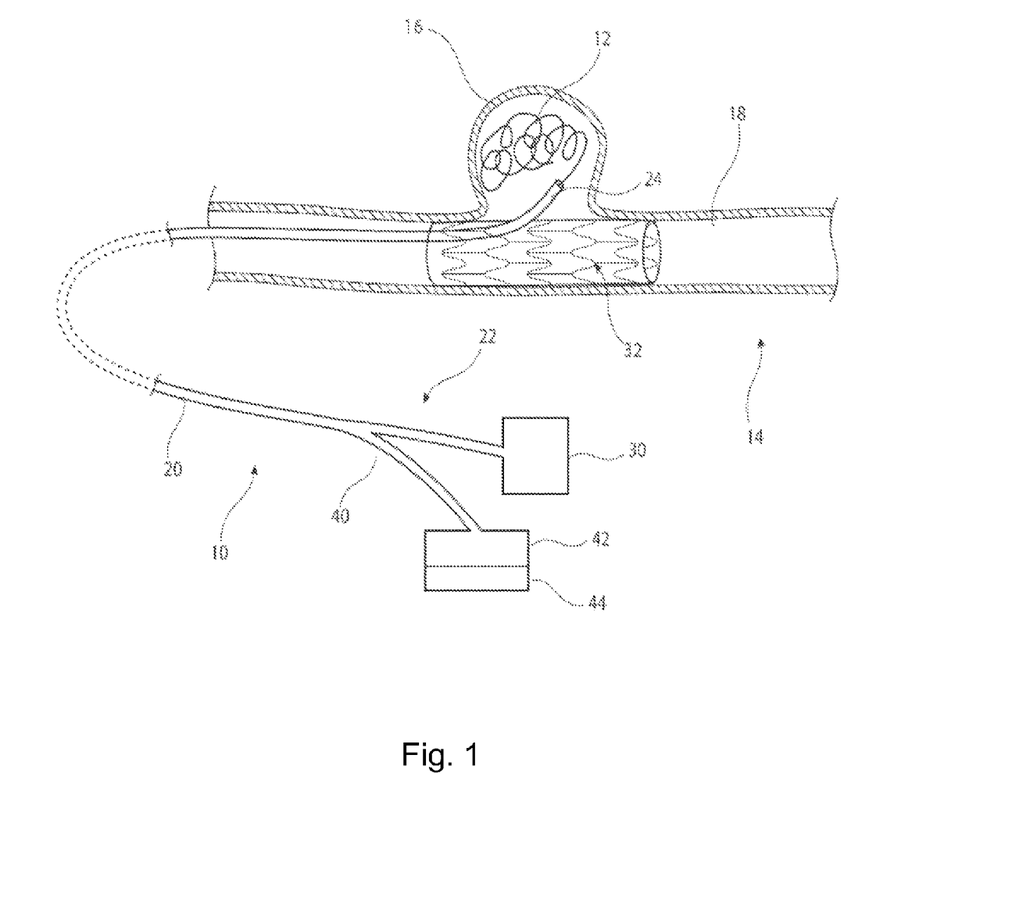
FIG. 1 is a schematic diagram of an embodiment of material feed apparatus according to an embodiment of the invention.

Referring to FIG. 1, this shows in schematic form an embodiment of material delivery device 10 in the course of delivering filamentary material 12 into a patient's vessel 14 and in particular into the sac 16 of an aneurysm formed in the vessel wall 18. Such an aneurysm occurs as a result of weakening of the vessel wall 18, which then expands outwardly in a bulge to form a sac 16. If left untreated, the walls of the sac 16 will continue to weaken as a result of continuing blood flow into and blood pressure on the sac 16, with possibly eventual rupture of the vessel wall and haemorrhaging.

The apparatus 10 includes a catheter 20 having a proximal end 22 and a distal end 24, the distal end being locatable in the patient's vessel 14 and in in the example application shown in the opening to the aneurysm sac 16. A source 30 of filler material is coupled to the proximal end 22 of the catheter 20 for feeding material 12 through the lumen of the catheter 20 and out of the distal end 24, so as to fill the volume of the aneurysm sac 16 this material.

There is a wide variety of biocompatible materials which can be used to fill the aneurysm sac 16. The preferred material is SIS (small intestine submucosa), preferred as this can be bioresorbed into the tissue of the vessel wall and eventually assist in remodelling of the vessel wall. A variety of other materials may be fed through the catheter 20 including, for example, polysaccharide or other biocompatible polymeric thread. Examples of suitable materials include, but are not limited to: woven polyester (such as Dacron®), polyamide such as Nylon, expanded polytetrafluoroethylene (such as Gore-Tex®), or bioremodelable materials such as: extracellular matrix material, for instance a submucosa, renal capsule membrane, dermal collagen, dura mater, pericardium, fascia lata, serosa, peritoneum and basement membrane layers. Examples of suitable submucosa include: intestinal submucosa, including small intestinal submucosa; stomach submucosa; urinary bladder submucosa and uterine submucosa.

The material from the material feed 30 could be of fibrous or filamentary form, such as a thread, which is continuous and of a length determined to be sufficient to fill the aneurysm sac 16, typically by between 20% to 40% of the volume of the sac. The proportion of the volume of the aneurysm sac which is filled is not material to this disclosure. It is also not excluded that discrete lengths of material may be fed through the catheter 20, in which case it would not be necessary to provide for cutting of the material.

The method of this example also involves deploying a stent 32 in the vessel 14 across the aneurysm 16, which has the effect of providing a support for any material fed into the aneurysm and also for assisting in the retention of the distal end 24 of the catheter 20 in the aneurysm sac during the material feeding process. In practice, a guide wire is fitted through one of the interstices in the elements of the stent, into the aneurysm sac 16 and then the catheter 20 is slid over the guide wire until its distal end 24 passes through the stent structure. For this purpose, the stent may have any suitable structure and may be formed of interconnected stent rings or may be a braiding, for example.

The assembly 10 also includes a side feed 40 disposed close to or at the proximal end 22 of the catheter 20 and which is coupled to a supply of 42 of driving fluid, under the control of a fluid pump 44, both described in further detail below. Saline solution is as suitable fluid for such purposes. The side feed 40 supplies driving fluid into the lumen of the catheter 20 under pressure, which has the effect of pulling material from the material feed 30 through the catheter 20 to the distal end 24 thereof. This is achieved by the force of the fluid flow on the material disposed in the lumen in the catheter 20.

The components of the preferred embodiments of the assembly 10 are described below, particularly with reference to FIGS. 2 to 5.

Figure 2:
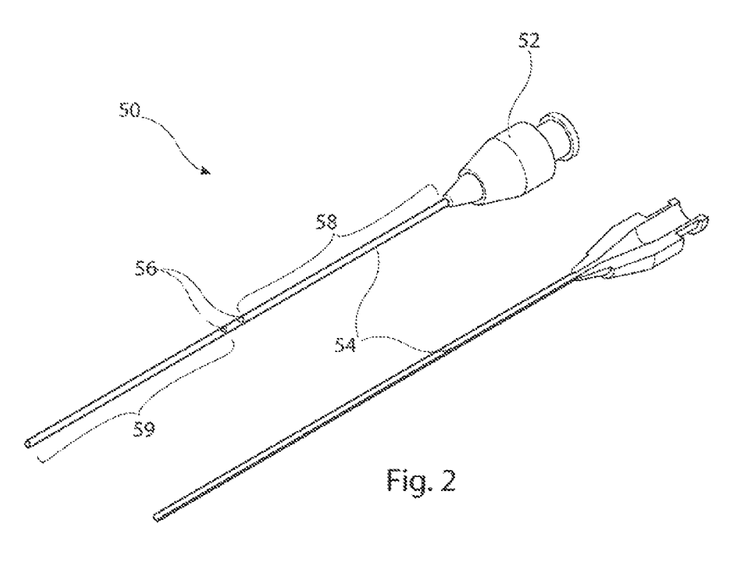
FIG. 2 is a side elevational view of an embodiment of carrier cannula of the embodiment of apparatus of FIG. 1.

Referring first to FIG. 2, this shows a cannula 50 provided at a proximal end thereof with a fitting 52, preferably a male luer fitting. The fitting 52 is selected to be compatible with a corresponding fitting at the outlet of the material source 30, in this example with a female luer fitting. The cannula 50 includes an elongate tubular element 54 having a lumen therein and, in this embodiment, a plurality of apertures 56 through the wall of the tubular element 54. In the example in FIG. 2, there are provided four apertures 56, two on each opposing side of the cannula (and hence only two are visible in FIG. 2), although in other embodiments there could be fewer or more than four apertures. The apertures 56 are preferably spaced from the proximal end of the cannula 50 by a distance 58 and by a distance 59 from the distal end of the cannula 50, described in further detail below.

The cannula 50 made of a substantially rigid material, such as metal or a hard plastic material, but may equally be made of a flexible material, preferably a suitable polymer.

Figure 3:
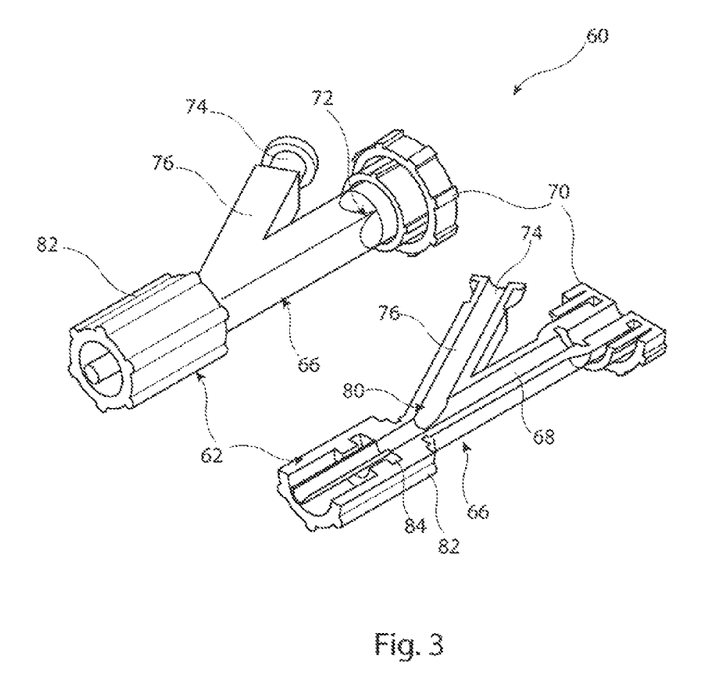
FIG. 3 is a side elevational view of an embodiment of Y-connector incorporating a side feed in accordance with the embodiment of apparatus of FIG. 1.

Referring now to FIG. 3, the apparatus 10 includes, in this embodiment, a Y-fitting 60 which in practice is coupled at its distal end 62 to the proximal end 22 of the catheter 20. This is achieved by provision of the female luer fitting 64 which engages with a corresponding male luer fitting (not shown) at the proximal end 22 of the catheter 20. The Y-fitting 60 includes a first branch 66 having a lumen 68 which in practice is aligned with the lumen of the catheter 20, forming a lumen through the assembly 10 for the passage of filler material. The first branch 68 includes a closure element 70 for attachment to a corresponding fitting provided on the material source 30, in one example connecting together by a screw fitting. The closure element 70 includes an aperture for the passage of the cannula 50 and is provided with a seal 71, such as an O-ring seal, visible in FIG. 6. A second branch 72 of the Y-fitting 60 includes at a proximal end thereof a male luer connector 74 for coupling to the drive fluid supply 42 and has a side lumen 76 therein which connects at a junction 80 with the central lumen 68 of the Y-fitting 60 and thus with the lumen of the catheter 20. A head portion 82 of the Y-Fitting 60 includes a seal 84 which extends into the lumen 68, in practice within a gap between two sections of the lumen 68 of the fitting 60. The seal 84 could usably be an O-ring seal.

Figure 4:
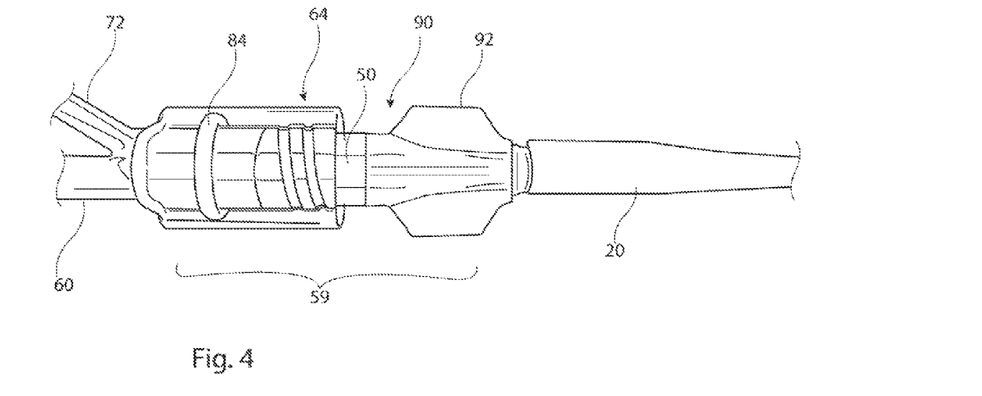
FIG. 4 is a side elevational view of an example of catheter coupling for the embodiment of apparatus of FIG. 1.

Referring now to FIG. 4, this shows the female luer connector 64 of the Y-fitting 60 coupled to a male luer fitting 90 fixed to the proximal end of the catheter 20. The male luer fitting 90 is provided with butterfly gripping elements 92 for assisting in the attachment and detachment of the luer fitting 90 to the Y-fitting 60. As can be seen, the distal end of the cannula 50 extends into the Y-fitting 60 and is held in position by abutment with the inner surface of the Y-fitting 60, thereby to ensure that the apertures 56 are aligned preferably at or downstream of the point at which the side branch 72 couples to the main branch 66 of the Y-fitting 60.

Figure 5:
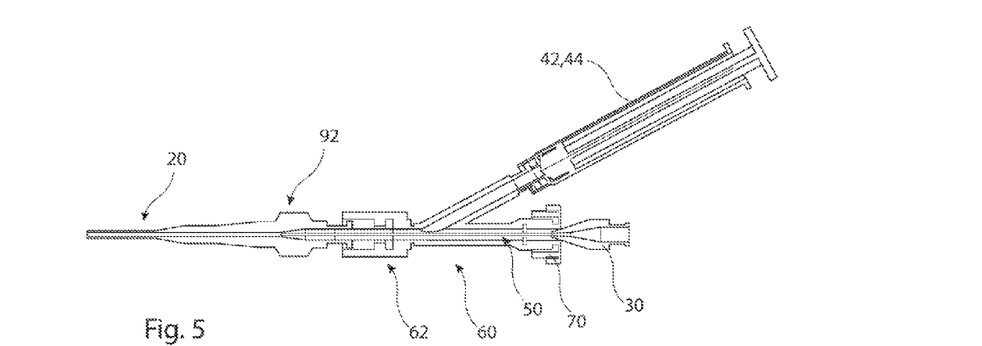
FIG. 5 is a side elevational view of a distal end of the assembly of FIGS. 1 to 4 in assembled form.

The proximal end of the assembly in its assembled form can be seen in FIG. 5, to which reference is now made. The Y-fitting 60 is coupled to the catheter 20 in the manner shown in FIG. 4. The cannula 50 is shown inserted into the proximal end of the main branch 68 of the Y-fitting 60 and to extends through the seal 84 and into the luer fitting 90 of the catheter assembly 20. The arrangement is such that the distance 58 to the apertures 56 is the same as the length of the main branch 66 to the junction with the side branch 72 or just downstream of this and before the O-ring seal 84. This ensures that the apertures 56 in the tubular element 54 are aligned with or positioned just downstream of the junction 80 of the two lumens 68, 76 of the two branches 66 and 72 of the Y-fitting 60 and just above the position of the seal 84. The skilled person will appreciate that only one of the positioning distances 58, 59 need be used to ensure correct positioning of the holes 56.

When so assembled and connected to a source of material (not shown), the lumen 68 of the branch 66 forms a sealed chamber in the Y-fitting, closed at one end by the closure element 70 and its seal 71 and at the other end by the seal 84. Thus, any fluid pumped into the side branch 76 will enter this chamber and under fluid pressure pass through the apertures 56 in the cannula 50, thereby generating fluid streams or jets into the interior of the cannula 50.

FIG. 5 also shows the driving fluid supply and pump 42 and 44, which in this embodiment are in the form of a syringe. The cylinder of the syringe acts as the driving fluid chamber and the piston of the syringe as the pump for driving the fluid into the side branch lumen 76 and thus into the primary lumen 68 of the Y-fitting 60 and then into the lumen of the catheter 20.

Figure 6:
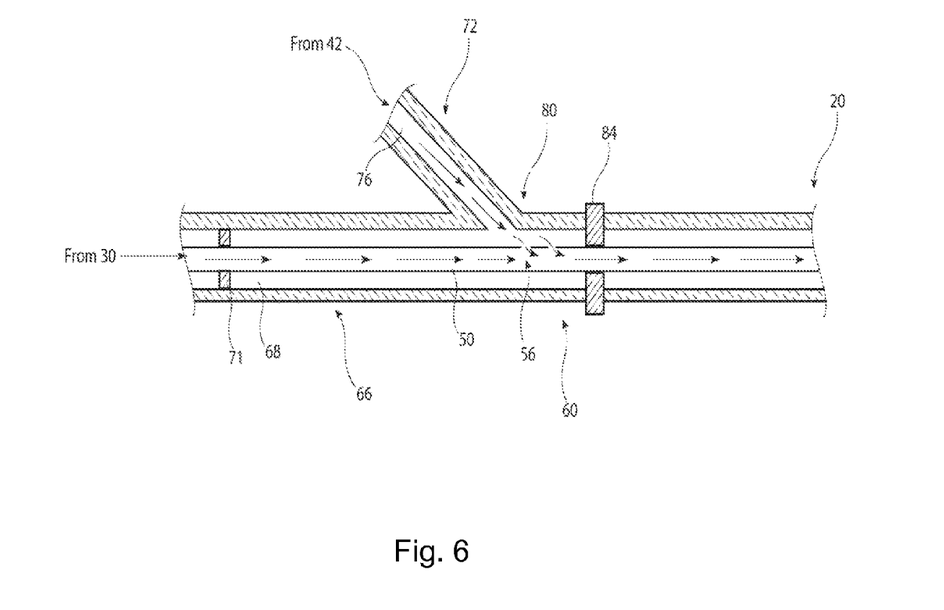
FIG. 6 is a schematic view in cross-section of the assembly of FIG. 5.

The internal arrangement of the device when assembled can be seen more clearly in the cross-sectional schematic view of FIG. 6, which shows a part of the assembly of FIG. 3. As can be seen, fluid from the drive fluid source 42 passes through the lumen 76 of the side branch 72 and into the primary lumen 68 of the main branch 66 of the fitting 60. As a result of the sealing action of the O-ring seals 71 there is formed a sealed chamber in the lumen 68 able to maintain fluid pressure. Thus, drive fluid is forced under pressure through the apertures 56 in the cannula 50, where material to be dispensed is supplied from the material supply 30. The flow of the fluid into the cannula acts to pull the material 12 within the lumen of the cannula 50 towards and then out of the distal end 24 of the catheter 20, thereby to deliver the material to the treatment site.

The apertures 56 in the cannula 50 could usefully be oriented in the distal direction, that is in the direction of flow, to enhance the flow of the driving fluid into and through the cannula, but this is not essential.

The provision of the cannula 50 and the drive fluid from the side branch 72 provides a very efficient material drive mechanism which can pull significant lengths of material through the catheter 20 in short periods of time while at the same time minimising the amount of drive fluid which is necessary. It has been found that this arrangement, compared to one which provides drive fluid from the location of the material source and though a single ended catheter, can be substantially improved. In particular, it is possible to deliver therapeutically sufficient quantities of material into a vessel or aneurysm within a period of seconds and in some cases of about one second only. A therapeutically sufficient quantity may be enough to fill an aneurysm sac or to occlude a vessel. As explained above, in practice the aneurysm sac is deemed full when the volume of delivered material is generally between 20% to 40% of the volume of the sac. The remaining volume of the sac will promote clotting of the blood held therein.

It will be appreciated that in several embodiments it is not necessary to provide a cannula such as a cannula 50 and in these embodiments the material may be fed directly though the central lumen 68 of the Y-fitting 60. It will also be appreciated that it is not necessary to have a separate Y-filling as taught herein as in other embodiments a double ended catheter could be used, such a catheter including a side branch equivalent to the side branch 72. However, a Y-fitting of the type disclosed herein is preferred as it allows convenient deployment over the wire, together with improved sterilisation and transport/storage of the assembly.

Similarly, although the preferred embodiment makes use of an O-ring seal to create a sealed chamber within the Y-fitting which provides for directing the drive fluid through the apertures 56 and the cannula 50, similar embodiments need not use a seal 84, relying instead on a flow of fluid into the lumen of the catheter 20 (in which the case the cannula 50 in its entirety may be omitted). However, this solution would require more drive fluid and may not drive material though the catheter and out of the distal end 24 as fast as the preferred embodiments described herein.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1320830.1, from which this application claims priority, and in the abstract accompanying this application are incorporated herein by reference.

We claim:

1. An assembly for delivering material into a patient including:
   an introducer unit having a proximal end, a distal end and a lumen extending within the introducer unit from the proximal to the distal ends;
   a side feed located at a position between the proximal and distal ends of the introducer unit and in fluid communication with the lumen;
   a material source coupled at the proximal end of the introducer unit, material thereof being passable through the lumen to the distal end of the introducer unit;
   a cannula disposed in the introducer unit at the proximal end thereof, the cannula comprising a side wall and being coupled to the material source, the cannula comprising at least one aperture through the side wall;
   a driving fluid source coupled to the side feed; and
   a seal disposed within the lumen and downstream of the at least one aperture, defining a sealed chamber within the lumen and in communication with the at least one aperture;
   wherein supply of driving fluid through the side feed and the sealed chamber is forced under pressure through the at least one aperture and causes material in the lumen to be pulled towards and out of the distal end of the introducer unit.

2. The assembly according to claim 1, wherein the side feed is disposed adjacent the proximal end of the introducer unit.

3. The assembly according to claim 1, wherein the introducer unit has a longitudinal axis and the side feed is oriented at an acute angle to the longitudinal axis.

4. The assembly according to claim 1, wherein the introducer unit includes a catheter and a Y-fitting coupled to the catheter, wherein one branch of the Y-fitting provides a proximal portion of the lumen, the lumen being formed by said one branch and a lumen of the catheter, and a second branch of the Y-fitting provides the side feed.

5. The assembly according to claim 1, wherein the cannula extends beyond a junction of the side feed and the lumen.

6. The assembly according to claim 1, wherein the cannula is shorter than the introducer unit.

7. The assembly according to claim 1, wherein the driving fluid source includes a fluid pump.

8. The assembly according to claim 1, wherein the material is SIS, polysaccharide, a biocompatible polymeric thread or other biocompatible material.

9. Apparatus for delivering material into a patient including:
   an introducer unit having a proximal end, a distal end and a lumen extending within the introducer unit from the proximal to the distal ends;
   a side feed located at a position between the proximal and distal ends of the introducer unit and in fluid communication with the lumen;
   the proximal end of the introducer unit being couplable to a material source such that material from the source is passable through the lumen to the distal end of the introducer unit;
   a cannula disposed in the introducer unit at the proximal end thereof, the cannula comprising a side wall and being able to be coupled to the material source, the cannula comprising at least one aperture through the side wall;
   a seal disposed within the lumen and downstream of the at least one aperture, defining a sealed chamber within the lumen and in communication with the at least one aperture;
   the side feed being couplable to a driving fluid source, wherein supply of driving fluid through the side feed and the sealed chamber is forced under pressure through the at least one aperture and causes material in the lumen to be pulled towards and out of the distal end of the introducer unit;
   driving fluid being able to pass into the cannula through said at least one aperture.

10. The apparatus of claim 9, wherein the introducer unit includes a catheter and a Y-fitting coupled to the catheter, wherein one branch of the Y-fitting provides a proximal portion of the lumen, the lumen being formed by said one branch and a lumen of the catheter, and a second branch of the Y-fitting provides the side feed.

11. The apparatus according to claim 9, wherein the cannula extends beyond a junction of the side feed and the lumen.

12. A method of delivering material into a patient by means of apparatus including an introducer unit having a proximal end, a distal end and a lumen extending within the introducer unit from the proximal to the distal ends; a side feed located at a position between the proximal and distal ends of the introducer unit and in fluid communication with the lumen; and a seal disposed within the lumen and downstream of at least one aperture formed in a side wall of an inner member contained within the introducer unit, defining a sealed chamber within the lumen and in communication with the at least one aperture; the method including the steps of:

feeding a material from a material source coupled at the proximal end of the introducer unit, said material passing through the lumen to the distal end of the introducer unit; and     driving a fluid through the side feed and through the at least one aperture, said driving fluid causing material in the lumen to be pulled towards and out of the distal end of the introducer unit.

13. The method according to claim 12, including the step of using a syringe to provide said driving fluid.

14. The method according to claim 12, wherein said material is fed through the introducer unit into a vessel or organ of a patient to close at least a part of said vessel or organ.

15. The method according to claim 12, wherein said material is fed into an aneurysm sac.

16. The method according to claim 12, wherein the material is SIS, polysaccharide, a biocompatible polymeric thread or other biocompatible material.

\* \* \* \* \*